United States Patent
Jorgensen et al.

(10) Patent No.: US 8,391,997 B2
(45) Date of Patent: Mar. 5, 2013

(54) EXTENDABLE/RETRACTABLE LEAD WITH IMPROVED DISTAL SEAL

(75) Inventors: Kimberly A. Jorgensen, Minneapolis, MN (US); Daniel J. Foster, Lino Lakes, MN (US); Bryan A. Clark, Coon Rapids, MN (US); Arthur J. Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 350 days.

(21) Appl. No.: 12/818,691

(22) Filed: Jun. 18, 2010

(65) Prior Publication Data

US 2010/0331943 A1 Dec. 30, 2010

Related U.S. Application Data

(60) Provisional application No. 61/221,704, filed on Jun. 30, 2009.

(51) Int. Cl.
*A61N 1/375* (2006.01)

(52) U.S. Cl. .......... 607/127; 607/37; 607/119; 607/122; 607/126

(58) Field of Classification Search .......... 607/127, 607/37
See application file for complete search history.

(56) References Cited

U.S. PATENT DOCUMENTS

| 5,456,708 | A * | 10/1995 | Doan et al. ............ 607/127 |
| 6,240,321 | B1 | 5/2001 | Janke et al. |
| 6,813,521 | B2 * | 11/2004 | Bischoff et al. ........ 607/122 |
| 6,931,285 | B2 | 8/2005 | Bischoff |
| 2007/0225772 | A1 * | 9/2007 | Lahti et al. ............ 607/37 |
| 2010/0305672 | A1 | 12/2010 | Felling et al. |

\* cited by examiner

*Primary Examiner* — Christopher D Koharski
*Assistant Examiner* — Michael Carey
(74) *Attorney, Agent, or Firm* — Faegre Baker Daniels LLP

(57) ABSTRACT

An implantable lead may have a distal assembly including a coupler, a fixation helix secured to the coupler and a housing in which the fixation helix and the coupler are disposed. The distal assembly may include an annular seal that is disposed between the coupler and the housing and that provides an at least substantially fluid-tight seal between the coupler and the housing.

14 Claims, 8 Drawing Sheets

EXTENDABLE/RETRACTABLE LEAD WITH IMPROVED DISTAL SEAL

CROSS-REFERENCE TO RELATED APPLICATION

This application claims the benefit under 35 U.S.C. §119 (e) to U.S. Provisional Patent Application No. 61/221,704, filed on Jun. 30, 2009, entitled "Extendable/Retractable Lead with Improved Distal Seal," which is incorporated herein by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Example 1 is an implantable lead having a flexible body, a connector assembly that is secured to a proximal end of the body for coupling the lead to an implantable medical device, a conductor member disposed longitudinally within the body and a distal assembly coupled to a distal end of the body. The connector assembly includes a terminal pin that is rotatable relative to the body. The conductor member is coupled to the terminal pin and is rotatable relative to the body. The distal assembly includes a housing having a distal region and a proximal region, the proximal region fixedly coupled to the distal end of the body. A coupler is rotatably disposed within the housing, the coupler having a proximal end and a distal end, the proximal end of the coupler is connected to the conductor member and the distal end of the coupler is fixedly secured to a helical electrode. An annular seal is disposed between the coupler and the housing such that the annular seal provides an at least substantially fluid tight seal between the coupler and the housing. The annular seal includes an annular base portion, an annular wiper portion and a central portion that extends between the base portion and the wiper portion. The annular base portion and the annular wiper portion extend axially beyond the central portion to define an annular channel between the annular base portion and the annular wiper portion. The terminal pin is rotatably engaged with the coupler via the conductor member such that rotation of the terminal pin causes the coupler and the helical electrode to rotate and therefore translate relative to the housing.

In Example 2, the implantable lead of Example 1 in which the coupler includes a sealing groove having a bottom surface, and the annular seal is disposed within the sealing groove such that the annular base portion seats against the bottom surface and the annular wiper portion sealingly engages the inner surface of the housing.

In Example 3, the implantable lead of Example 2 in which the housing includes a sealing groove having a bottom surface and the annular seal is disposed within the sealing groove such that the annular base portions seats against the bottom surface and the annular wiper portion sealingly engages the outer surface of the coupler.

In Example 4, the implantable lead of any of Examples 1-3 in which the annular seal includes silicone rubber.

In Example 5, the implantable lead of any of Examples 1-4 in which the annular seal is disposed such that the annular groove faces the distal region of the housing.

In Example 6, the implantable lead of Example 5 in which the annular seal is configured such that fluid flow into the annular channel applies a sealing force to the annular wiper portion.

In Example 7, the implantable lead of Example 6 in which the central portion of the annular sealing portion partially defines the annular channel.

Example 8 is an implantable lead that is configured to carry an electrical signal. The implantable lead includes a flexible body that extends between a proximal end and a distal end, and that is configured to carry an electrical signal from the proximal end to the distal end. A distal assembly is coupled to the distal end of the body. The distal assembly includes a housing having a distal region and a proximal region that is fixedly coupled to the distal end of the body. A coupler having a proximal region and a distal region is rotatably disposed within the housing, the coupler including a sealing groove that is disposed within the distal region and that includes a bottom surface. A fixation helix is attached to the coupler. An annular seal is disposed within the sealing groove such that the annular seal provides an at least substantially fluid tight seal between the coupler and the housing. The annular seal includes an annular base portion seated against the bottom surface of the sealing groove, an annular wiper portion sealingly engaged with the inner surface of the housing, and a central portion extending between the base portion and the wiper portion, the annular base portion and the annular wiper portion extending axially beyond the central portion to define an annular channel between the annular base portion and the annular wiper portion.

In Example 9, the implantable lead of Example 8 in which the annular base portion includes a flat side seated against the bottom surface of the sealing groove and an angled side extending obliquely relative to the flat side, the angled side partially defining the annular channel.

In Example 10, the implantable lead of Example 8 or Example 9 in which the annular base portion has a width parallel to the bottom surface of the sealing groove that is greater than a height of the annular seal measured perpendicular to the bottom surface of the sealing groove.

In Example 11, the implantable lead of Example 10 in which the bottom surface of the sealing groove has a width that is greater than or equal to the width of the annular base portion parallel to the bottom surface of the sealing groove.

In Example 12, the implantable lead of any of Examples 8-11 in which the annular wiper portion includes a first angled side facing towards the inner surface of the housing and a second angled side that partially defines the annular channel.

In Example 13, the implantable lead of any of Examples 8-12 in which the first angled side of the annular wiper portion includes a sealing surface that sealingly engages the inner surface of the housing, the sealing surface extending along a portion of the first angled side.

In Example 14, the implantable lead of Example 13 in which the annular seal is molded such that the sealing surface is free of parting lines.

In Example 15, the implantable lead of Example 14 further including a lubricious coating on the sealing surface.

Example 16 is an implantable lead that is configured to carry an electrical signal. The implantable lead includes a flexible body that extends between a proximal end and a distal end, and that is configured to carry an electrical signal from the proximal end to the distal end. A distal assembly is coupled to the distal end of the body. The distal assembly includes a housing having a distal region and a proximal region that is fixedly coupled to the distal end of the body. A coupler having a proximal region and a distal region is rotatably disposed within the housing, the coupler including a sealing groove that is disposed within the distal region and that includes a bottom surface. A fixation helix is attached to the coupler. A duplex seal is disposed between the coupler and the housing. The duplex seal includes a first annular seal portion facing the distal end of the housing and a second annular seal portion facing away from the distal end of the housing.

In Example 17, the implantable lead of Example 16 in which the second annular seal portion includes a second annular base portion, a second annular wiper portion and a second central portion extending between the second annular base portion and the second annular wiper portion. The second annular base portion and the second annular wiper portion extend proximally beyond the second central portion to define a second annular channel between the second annular base portion and the second annular wiper portion.

In Example 18, the implantable lead of Example 16 or Example 17 in which the first annular seal includes a first annular base portion, a first annular wiper portion and a first central portion extending between the first annular base portion and the first annular wiper portion. The first annular base portion and the first annular wiper portion extend distally beyond the first central portion to define a first annular channel between the first annular base portion and the first annular wiper portion.

In Example 19, the implantable lead of any of Examples 16-18 in which the first annular seal portion and the second annular seal portion are molded as separate pieces.

In Example 20, the implantable lead of any of Examples 16-19 in which the first annular seal portion and the second annular seal portion are integrally molded together as the duplex seal.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
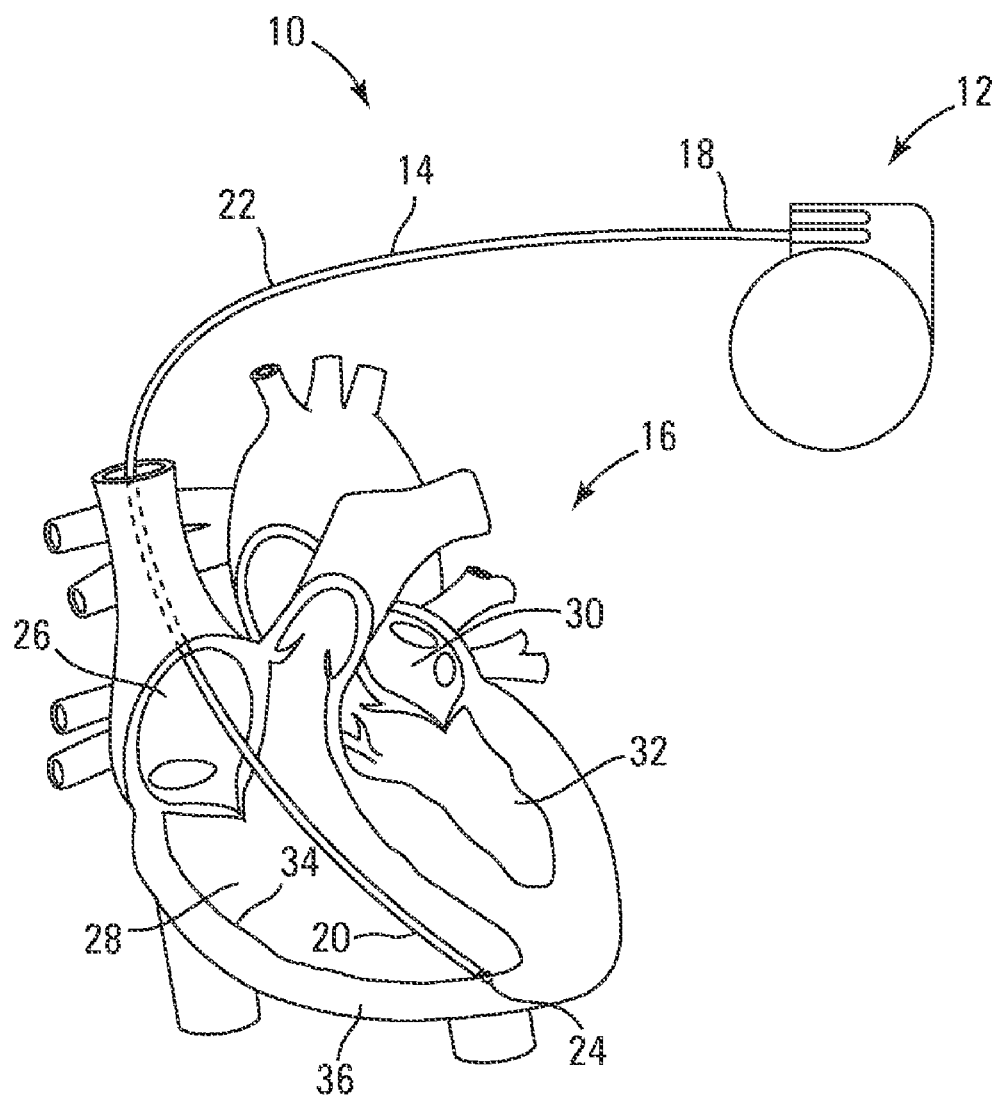
FIG. 1 is a combined cutaway and perspective view of an implantable medical device and lead in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes an extendable/retractable fixation helix 24, which as will be discussed in greater detail below locates and/or secures the distal region 20 within the heart 16. As will be explained in detail below, the distal region 20 of the lead 14 includes a seal arrangement providing a substantially fluid tight seal against fluid ingress. In addition, the seal arrangement is configured to seal the interior of the lead 14 while minimizing friction when advancing and/or retracting the fixation helix 24.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus can be used to sense the electrical activity of the heart 16 and/or to apply a stimulating pulse to the right ventricle 28. In other embodiments, the fixation helix 24 is not electrically active. Rather, in some embodiments, other components of the lead 14 are electrically active.

Figure 2:
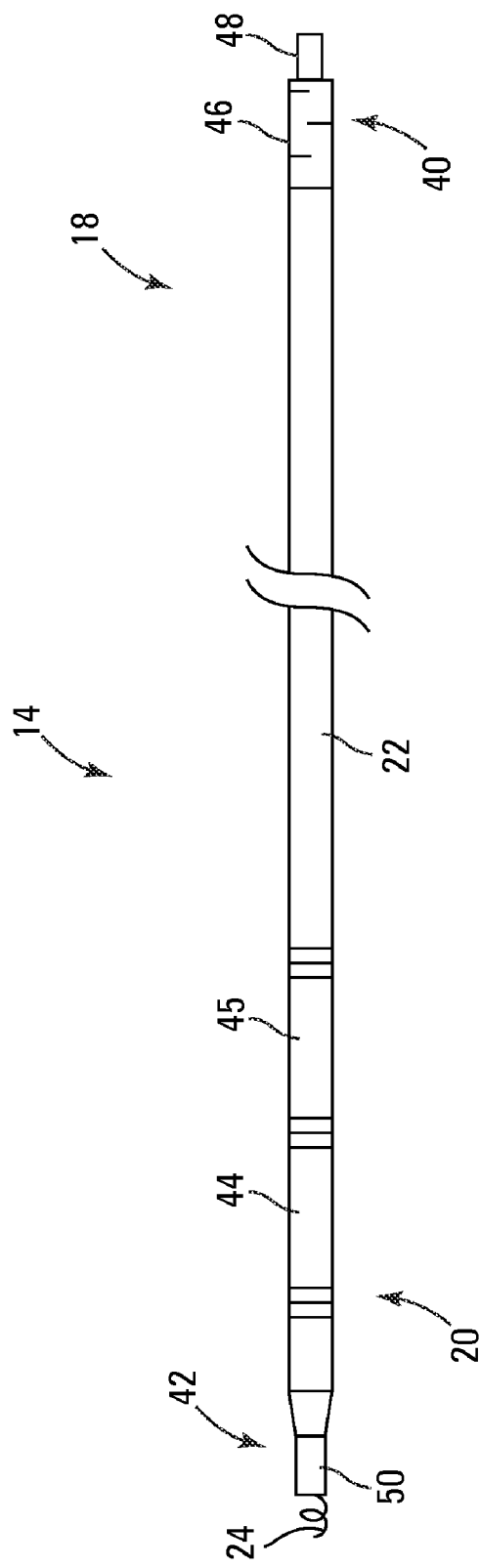
FIG. 2 is a side elevation view of the lead of FIG. 1.

FIG. 2 is an isometric illustration of the lead 14. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally within the lead body 22 and which is rotatable relative to the lead body 22 such that rotating the terminal pin 48 (relative to the lead body 22) causes the conductor member to rotate within the lead body 22 as well. In some embodiments, the terminal pin 48 includes an aperture extending therethrough, and the conductor member defines a longitudinal lumen in communication with the aperture. When present, the aperture and/or conductor lumen are configured to accommodate a guide wire or an insertion stylet for delivery of the lead 14.

The distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 may accommodate or include structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a pace/sense electrode. In some embodiments, the fixation helix 24 is made of an electrically conductive material such as Elgiloy, MP35N, tungsten, tantalum, iridium, platinum, titanium, palladium, stainless steel, as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

Figure 3A:
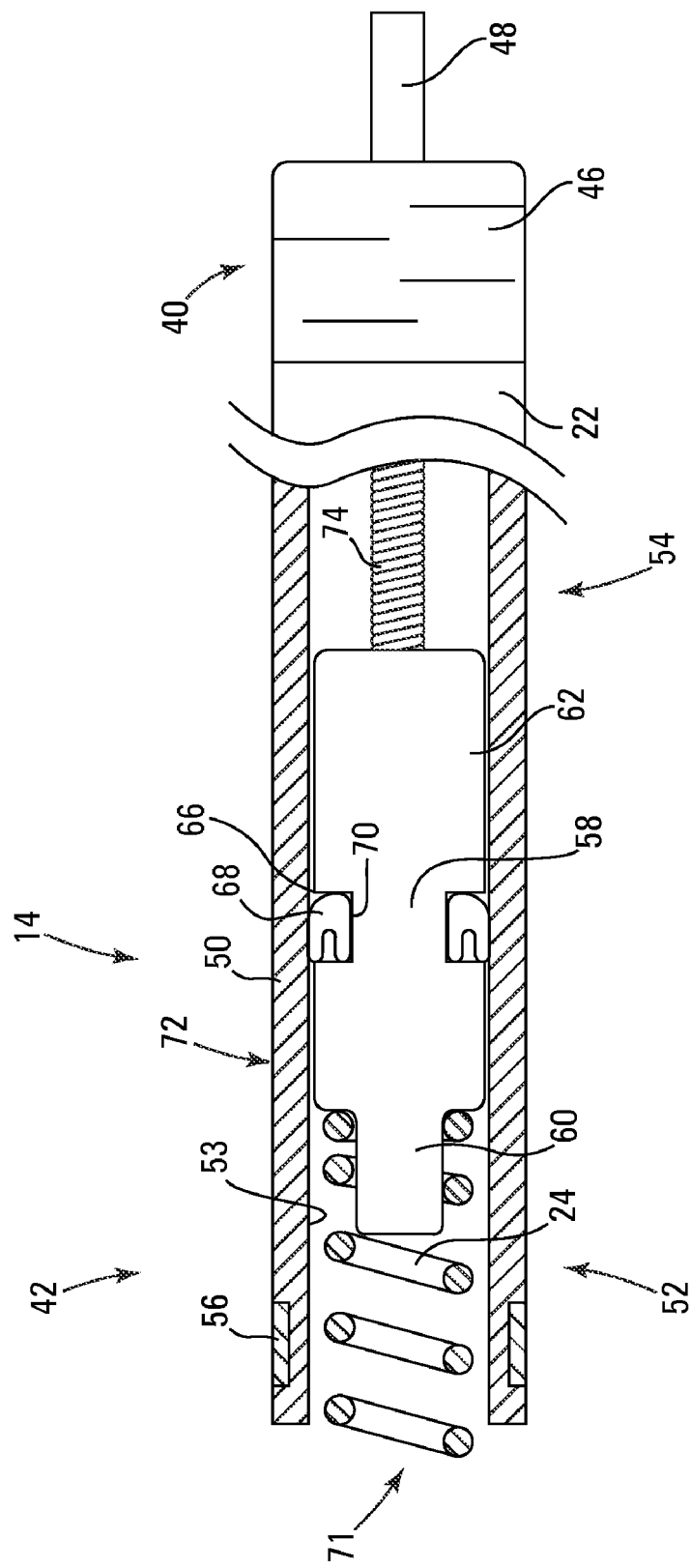
FIG. 3A is a partial cross-sectional view of the lead of FIG. 1, shown in a retracted position.
Figure 3B:
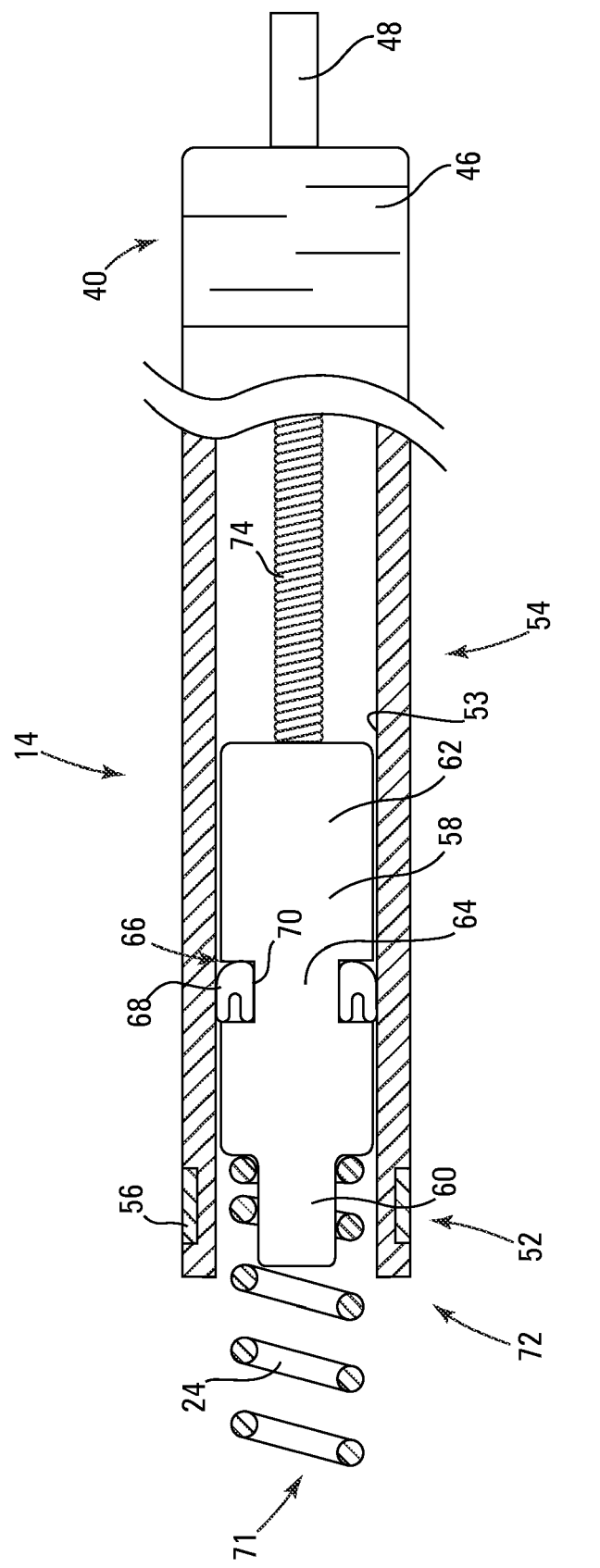
FIG. 3B is a partial cross-sectional view of the lead of FIG. 1, shown in an extended position.

FIGS. 3A and 3B illustrate an embodiment of a lead including distal assemblies in accordance with the present invention. FIGS. 3A and 3B are partial cross-sections of the lead 14 that include the distal assembly 42. In FIG. 3A, the fixation helix 24 is illustrated in a retracted position while FIG. 3B illustrates the fixation helix 24 in an extended position. In the illustrated embodiment, the fixation helix 24 is electrically active so as to be operable as a pace/sense electrode.

As shown in FIGS. 3A and 3B, the housing 50 includes a distal region 52 and a proximal region 54. The housing 50 has an inner surface 53. The housing 50 is, in general, relatively rigid or semi-rigid. In some embodiments, the housing 50 is made of an electrically conductive material such as Elgiloy, MP35N, tungsten, tantalum, iridium, platinum, titanium, palladium, stainless steel, as well as alloys of any of these materials. In some embodiments, the housing 50 is made of a non-electrically conductive material such as PES, polyurethane-based thermoplastics, ceramics, polypropylene and PEEK.

In the illustrated embodiment, a drug eluting collar 56 is disposed about an exterior of the housing 50 within the distal region 52. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments the distal assembly 42 may include a radiopaque element disposed under the drug eluting collar 56.

Figure 4:
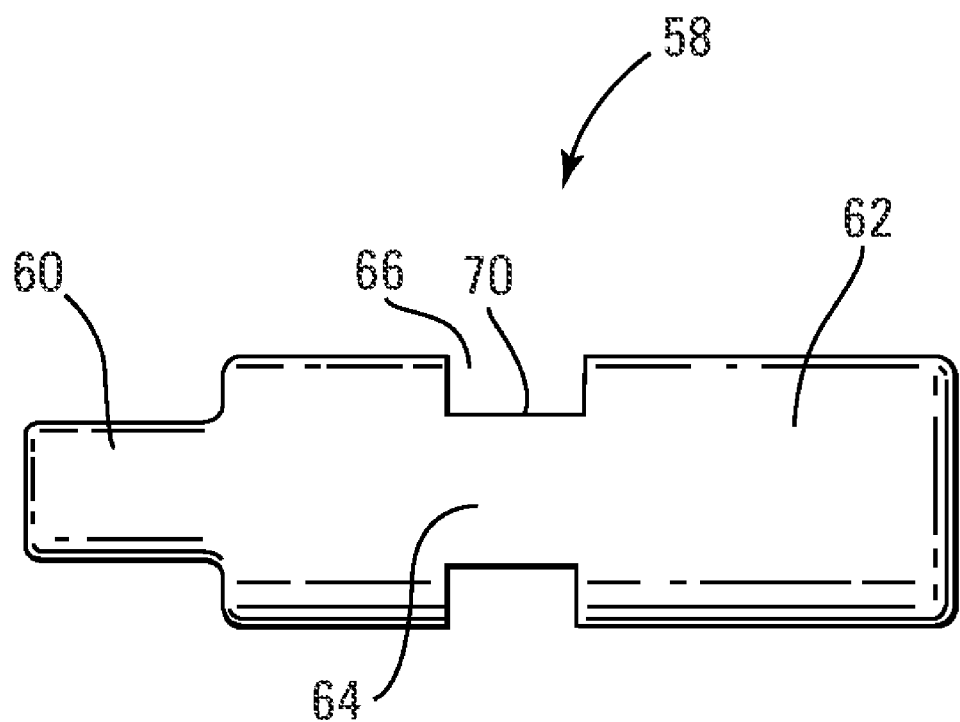
FIG. 4 is an enlarged view of a coupler visible in FIGS. 3A and 3B.

As shown, the distal assembly 42 includes a coupler 58. In some embodiments, the coupler 58 is formed of a metallic material and is configured to move longitudinally and/or rotationally with respect to the housing 50. As best illustrated in FIG. 4, the coupler 58 includes a distal portion 60, a proximal portion 62 and a central portion 64. As shown, the fixation helix 24 is connected to the distal portion 60 of the coupler 58. In some embodiments, as illustrated, the distal portion 60 may have a relatively smaller diameter (relative to at least part of the central portion 64) that is configured to accommodate the fixation helix 24.

In some embodiments, as illustrated, the central portion 64 of the coupler 58 includes a sealing groove 66 that is configured to accommodate an annular seal 68. The sealing groove 66 has a bottom surface 70 that, as will be described in detail below, provides a surface for the annular seal 68 to seat against. The annular seal 68 is configured to provide a substantially fluid-tight seal between the coupler 58 and the inner surface 53 of the housing 50 while minimizing frictional forces caused by the annular seal 68. The annular seal 68 is better illustrated in FIGS. 5-7, and thus will be discussed in greater detail subsequently with respect to these FIGS.

The fixation helix 24 has a distal region 71 and a proximal region 72. The proximal region 72 is secured to the distal portion 60 of the coupler 58. One or more attachment methods are used to secure the fixation helix 24 to the coupler 58. In some embodiments, the proximal region 72 of the fixation helix 24 is welded or soldered onto the distal portion 60 of the coupler 58. In some embodiments, the proximal region 72 of the fixation helix 24 has an inner diameter that is less than an outer diameter of the distal portion 60 of the coupler 58, and thus is held in place via compressive forces. In some embodiments, multiple attachment methods are used.

A conductor member 74 is secured to the proximal portion 62 of the coupler 58, and extends proximally through the lead body 22 to the connector assembly 40. In some embodiments, the conductor member 74 includes or is otherwise formed from a metallic coil. The coupler 58 provides an electrical connection between the conductor member 74 and the fixation helix 24. In the connector assembly 40, the conductor member 74 is coupled to the terminal pin 48 such that rotation of the terminal pin 48 causes the conductor member 74 to rotate. As the conductor member 74 rotates, the coupler 58 and the fixation helix 24 will also rotate. In some embodiments, the fixation helix 24 is rotated via a stylet that is inserted through an aperture that may be formed within the terminal pin 48 (FIG. 2). The distal assembly 42 is configured so that relative rotation of the coupler 58 and fixation helix 24 relative to the housing 50 results in longitudinal translation of the coupler 58 and fixation helix 24 relative to the housing 50, thereby providing the extendable/retractable functionality of the fixation helix 24.

The particular arrangement illustrated for facilitating extension and retraction of the fixation helix 24 is exemplary only. In other words, any arrangement, whether now known or later developed, for providing the extendable/retractable functionality of the fixation helix 24 can be utilized in connection with the various embodiments of the present invention. In one embodiment, the lead 14 includes structures such as those described and illustrated in co-pending and commonly assigned U.S. Provisional Patent Application 61/181, 954, the disclosure of which is incorporated by reference herein in its entirety. In other embodiments, a different arrangement for extending and retracting the fixation helix 24 is utilized.

Figure 5:
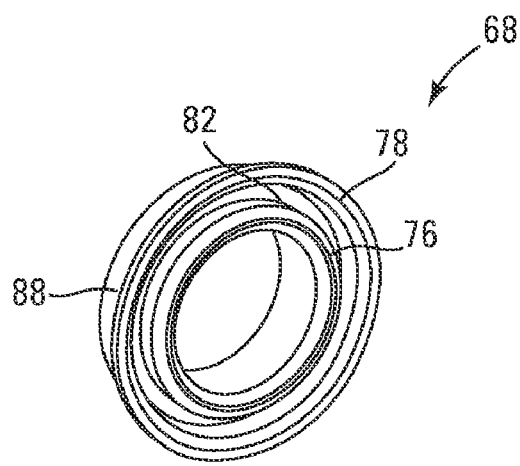
FIG. 5 is an enlarged isometric view of a seal visible in FIGS. 3A and 3B.
Figure 6:
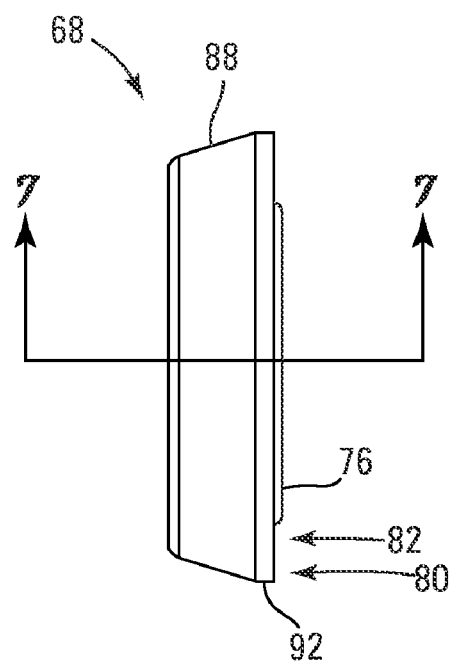
FIG. 6 is a side elevation view of the seal of FIG. 5.
Figure 7:
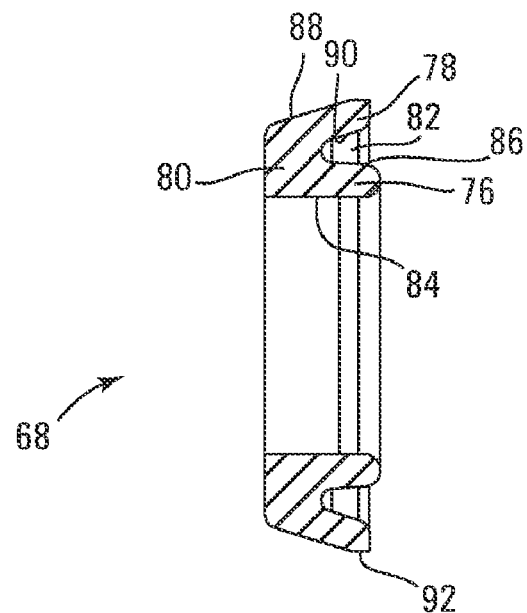
FIG. 7 is a cross-sectional view of the seal of FIG. 5, taken along line 7-7 of FIG. 6.

FIGS. 5 through 7 provide several views of the annular seal 68. FIG. 5 is an isometric view, FIG. 6 is a side elevation view and FIG. 7 is a cross-sectional view taken along line 7-7 of FIG. 6. In some embodiments, the annular seal 68 is molded from a material such as silicone rubber, polyurethane or a polyurethane/silicone copolymer. The material of the annular seal 68 may include one or more fillers or additives for tailoring the physical characteristics, e.g., radiopacity, lubriciousness, stiffness, and the like, of the annular seal 68. Examples of suitable fillers include but are not limited to one or more of barium sulfate, bismuth subcarbonate, titanium dioxide, PTFE (polytetrafluoroethylene) and metallic particles.

The annular seal 68 includes an annular base portion 76, an annular wiper portion 78 and a central portion 80 that extends between the annular base portion 76 and the annular wiper portion 78. In some embodiments, as illustrated, the annular base portion 76 and the annular wiper portion 78 extend axially beyond the central portion 80 to define an annular channel 82 that is disposed between the annular base portion 76 and the annular wiper portion 78.

In some embodiments, the annular base portion 76 includes a flat side 84 and an angled side 86 that is oriented at an oblique angle relative to the flat side 84. In some embodiments, the flat side 84 is sized and configured to seat against the bottom surface 70 of the sealing groove 66 while the angled side 86 partially defines the annular channel 82. In the illustrated embodiment, the annular wiper portion 78 includes a first angled side 88 that faces toward the inner surface 53 of the housing 50 and a second angled surface 90 that partially defines the annular channel 82.

In the illustrated embodiment, the first angled side 88 includes a sealing surface 92 that extends along a portion of the first angled side 88. In some embodiments, the sealing surface 92 extends along only a portion of the first angled side 88 in order to minimize friction between the sealing surface 92 and the inner surface 53 of the housing 50. In various embodiments, a lubricious coating may be applied to the sealing surface 92, if desired, to further reduce such frictional forces.

The annular seal 68 provides additional functionality to the lead 14. As discussed, the annular seal 68 is disposed between the coupler 58 and the housing 50 and provides a substantially fluid tight seal between the coupler 58 and the housing 50. The annular seal 68 is configured to seal the interior of the lead 14 while minimizing friction between the annular seal 68 and the inner surface 53 of the housing 50 when advancing and/or retracting the fixation helix 24. The annular seal 68 has a unique geometry that permits reduced compression and thus frictional forces are minimized. In some instances, fluid flow impinging on the annular wiper portion 78 increases sealing forces between the annular seal 68 and the inner surface 53 of the housing 50. In some embodiments, as illustrated for example in FIGS. 3A and 3B, the annular seal 68 may be disposed within the housing 50 such that the annular channel 82 faces distally, i.e., towards a distal end of the housing 50.

In some embodiments, as illustrated, the annular seal 68 is seated within the sealing groove 66 formed within the central portion 64 of the coupler 58. The annular base portion 76 is centrally located within the annular seal 68 such that, as discussed above, the annular base portion 76 seats against the bottom surface 70 of the sealing groove 66 while the annular wiper portion 78 is peripherally located within the annular seal 68 so that the sealing surface 92 sealingly engages the inner surface 53 of the housing 50. Alternatively, in other embodiments, the annular seal 68, and in turn, the mating elements of the housing 50 and the coupler 58, can take on other configurations.

For example, in various embodiments, the lead 14 may include a sealing groove formed within the inner surface 53 of the housing 50, and the annular seal 68 is seated within this sealing groove. In such embodiments, the annular seal 68 may be configured such that the annular base portion 76 is disposed about a periphery of the annular seal 68 while the annular wiper portion 78 is more centrally located so that it can sealingly engage an outer surface of the coupler 58. In this embodiment, the annular seal 68 is disposed within the sealing groove in an orientation in which the annular channel 82 formed between the annular base portion 76 and the annular wiper portion 78 faces the distal region 52 of the distal assembly 42.

It is contemplated that in some embodiments, the annular seal 68 may have two annular wiper portions. In this embodiment, an annular seal would have a first wiper portion centrally located to sealingly engage the coupler 58 and a second wiper portion peripherally located to sealingly engage the inner surface 53 of the housing 50. One of the wiper portions may be disposed within a sealing groove or, alternatively, the annular seal may be slidingly disposed between the coupler 58 and the housing 50 such that the annular seal can move relative to the coupler 58 and/or the housing 50.

Figure 8:
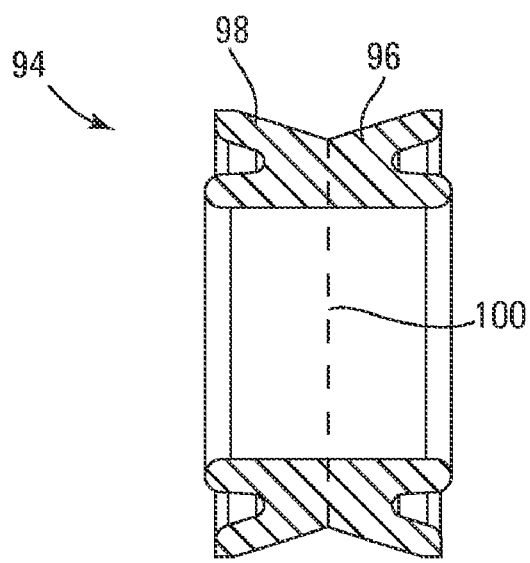
FIG. 8 is a schematic view of a duplex seal in accordance with an embodiment of the present invention.

FIG. 8 is a schematic view of a duplex seal 94 that in some ways may be considered as being formed by combining a first annular seal 96 back to back with a second annular seal 98. In some embodiments, each of the first annular seal 96 and/or the second annular seal 98 are similar in construction and other details to the annular seal 68 discussed above with respect to FIGS. 5-7. In some embodiments, the first annular seal 96 and the second annular seal 98 are separately formed (as indicated by a dashed line 100) and then are arranged back to back as illustrated. In some embodiments, the first annular seal 96 and the second annular seal 98 are integrally molded as a single polymeric structure.

It will be appreciated that the duplex seal 94 may be disposed within a sealing groove within a coupler. In some instances, each of the first annular seal 96 and the second annular seal 98 provide unique benefits to a lead. If, for example, the first annular seal 96 faces in a generally distal direction and the second annular seal 98 faces in a generally proximal direction, the first annular seal 96 may at least substantially prevent fluid inflow into the interior of the lead from the distal end thereof. The second annular seal 98 may, in this example, prevent fluid (such as air) within the interior of the lead from escaping distally. The first and second annular seals 96, 98 also provide a measure of redundancy without unduly increasing frictional drag between the housing and coupler.

Figure 9A:
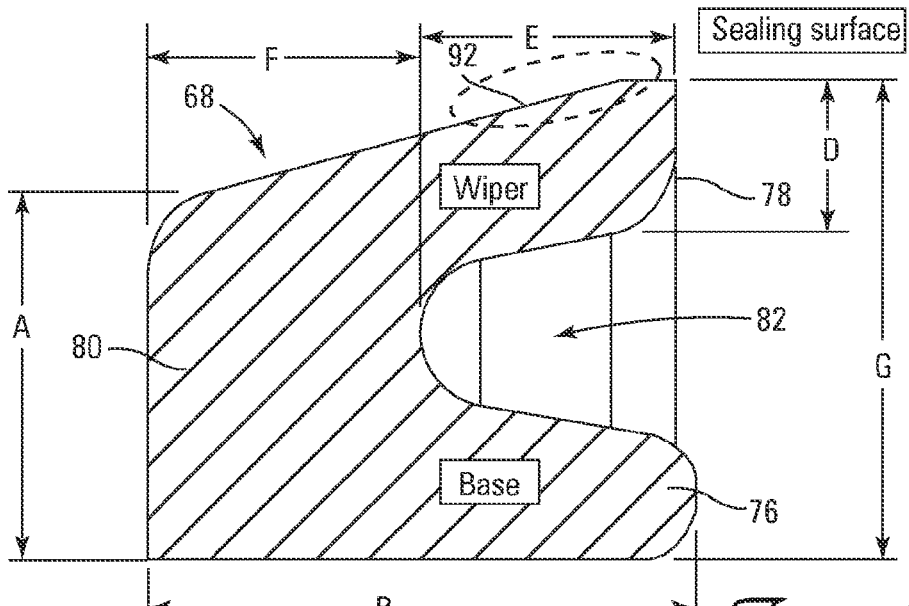
FIG. 9A is a schematic view of the seal of FIG. 5, illustrating particular dimensional relationships.
Figure 9B:
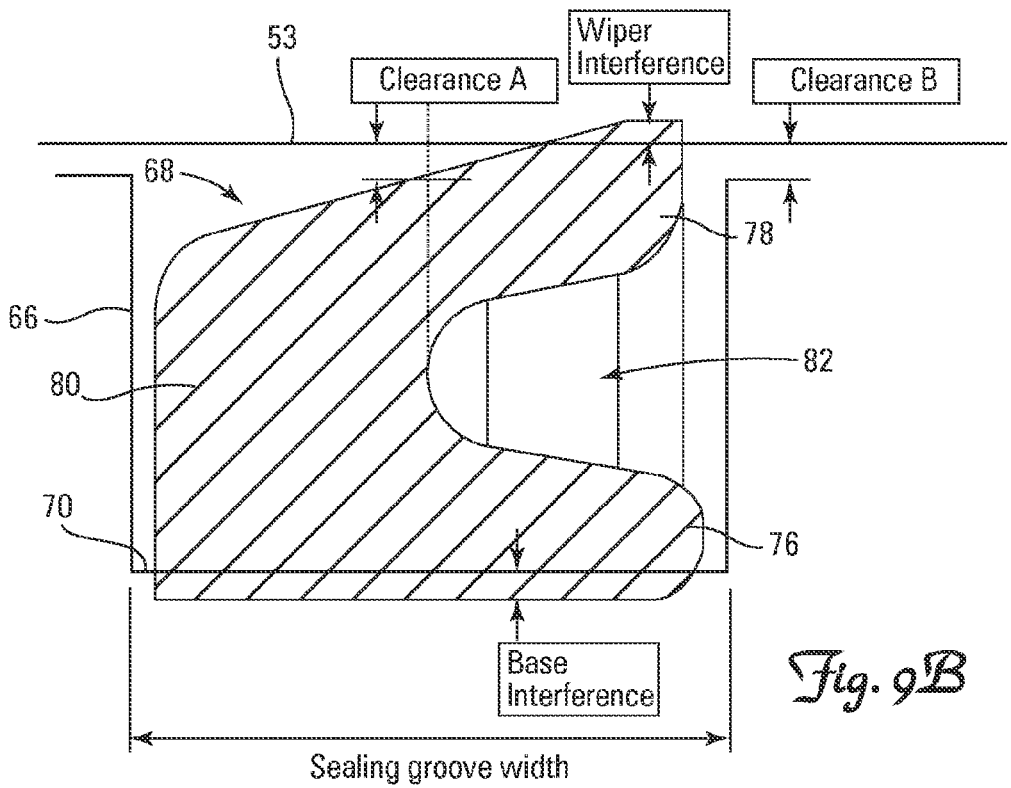
FIG. 9B is a schematic view of the seal of FIG. 5, superimposed over a portion of the coupler of FIG. 4, illustrating particular dimensional relationships therebetween.

The annular seal has a unique geometry that permits reduced compression and thus frictional forces are minimized. In some instances, fluid flow impinging on the seal actually increases sealing forces between the annular seal and the interior of the lead 14. FIG. 9A is a schematic view of the seal 68 of FIG. 5, illustrating particular dimensional relationships for the various elements of the seal 68 while FIG. 9B is a schematic view of the annular seal 68 of FIG. 5, superimposed over a portion of the coupler 58 of FIG. 4, illustrating particular dimensional relationships therebetween.

Dimension (Dim) A is roughly equal to a height of the central portion 80 while dimension F is about equal to a width of the central portion 80. Dimension D is roughly equal to an average thickness of the annular wiper portion 78 while the sum of dimension E and dimension F is about equal to an overall width of the annular wiper portion 78. Dimension E describes how far the annular wiper portion 78 extends axially beyond the central portion 80 and thus at least partially defines a depth of the annular channel 82. Dimension G is roughly equal to an overall height of the annular seal 68. Dimension B is roughly equal to a width of the base portion 76.

Clearance A describes a distance between the inner surface 53 of the housing 50 measured at an axial position corresponding to a point where the central portion 80 partially defines the annular channel 82. The wiper interference defines how far the annular wiper portion 78 extends (in a relaxed configuration) beyond the inner surface 53 of the housing 50, measured near the sealing surface 92. In other words, the wiper interference represents the difference between the largest outer radius of the annular seal 68 and the radius of the inner surface of the housing, and can be expressed as a percentage of the largest outer diameter of the annular seal 68. Clearance B describes a distance between the coupler 58 and the inner surface 53 of the housing 50. The base interference defines how far the annular base portion 76 (in a relaxed configuration) extends beyond the bottom surface 70 of the sealing groove 66. In other words, the base interference represents the difference between the radii of the inner surface of the annular seal 68 and the bottom surface 70 of the sealing groove 66, and can be expressed as a percentage of the inner diameter of the annular seal 68. The sealing groove width describes the width of the sealing groove 66.

In general, sealing efficiency will vary with varying wiper interference, with a relatively high wiper interference generally providing a relatively high sealing efficiency, and vice-versa. Similarly, frictional forces and corresponding drag between the housing and the coupler will also vary with wiper interference, such that a relatively high wiper interference will result in relatively high frictional forces and drag between these components. Thus, the wiper interference can be tailored to provide any desired combination of seal efficiency and frictional resistance to movement between the housing and the coupler. With respect to the base interference, there is a balance between securing the annular seal 68 within the sealing groove 66 and being able to physically place the annular seal 68 within the sealing groove 66. Useful relationships between these dimensions are outlined in the following table:

| Design Parameter | Fluid Sealing | Seal Stability | Reduces Friction | Processing | Other |
|---|---|---|---|---|---|
| Dim B > Dim A (1:1 to 2:1, target approx. 3:2) | | X | | | |
| Sealing groove width = 100% to 115% of Dim B | X | | X | X | |
| No parting lines or gates on sealing surface | X | | | X | |
| Dim F = 33% to 66% of Dim B | X | X | X | | |
| Base thickness ≧ 75% of Wiper thickness | X | X | X | | |
| Clearance A ≧ 0 | | | X | | |
| Clearance B < Dim D | | | | | Prevents rolling of seal into gap |
| Base Interference 0 to 10% | X | | | | |
| Wiper Interference 0 to 10% | X | | X | | |
| Dim F + Dim E 75% to 125% of Dim B | | X | | | |

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead comprising:
   a flexible body extending between a proximal end and a distal end;
   a connector assembly secured to the proximal end for coupling the lead to an implantable medical device, the connector assembly including a terminal pin rotatable relative to the body;
   a conductor member disposed longitudinally within the body and coupled to the terminal pin, the conductor member rotatable relative to the body; and
   a distal assembly coupled to the distal end of the body and including:
      a housing having a distal region and a proximal region, the proximal region fixedly coupled to the distal end of the body, the housing having an inner surface;
      a coupler rotatably disposed within the housing, the coupler having a proximal end, a distal end and an outer surface, the proximal end connected to the conductor member;
      a helical electrode fixedly secured to the coupler; and
      an annular seal disposed between the coupler and housing, the annular seal providing an at least substantially fluid tight seal between the coupler and the housing, the annular seal including:

an annular base portion;

an annular wiper portion; and a central portion extending between the base portion and the wiper portion, the annular base portion and the annular wiper portion extending axially beyond the central portion to define an annular channel between the annular base portion and the annular wiper portion, the annular seal being disposed and configured such that fluid flow into the annular channel applies a sealing force to the annular wiper portion;

wherein the terminal pin is rotatably engaged with the coupler via the conductor member such that rotation of the terminal pin causes the coupler and the helical electrode to rotate and therefore translate relative to the housing.

2. The implantable lead of claim 1, wherein the coupler includes a sealing groove having a bottom surface, and the annular seal is disposed within the sealing groove such that the annular base portion seats against the bottom surface and the annular wiper portion sealingly engages the inner surface of the housing.

3. The implantable lead of claim 1, wherein the housing includes a sealing groove having a bottom surface and the annular seal is disposed within the sealing groove such that the annular base portions seats against the bottom surface and the annular wiper portion sealingly engages the outer surface of the coupler.

4. The implantable lead of claim 1, wherein the annular seal comprises silicone rubber.

5. The implantable lead of claim 4, wherein the annular seal is disposed such that the annular channel faces the distal region of the housing.

6. The implantable lead of claim 1, wherein the central portion of the annular sealing portion partially defines the annular channel.

7. An implantable lead configured to carry an electrical signal, the implantable lead comprising:

a flexible body extending between a proximal end and a distal end, the body configured to carry an electrical signal from the proximal end to the distal end; and a distal assembly coupled to the distal end of the body and including:

a housing having a distal region, a proximal region and an inner surface, the proximal region fixedly coupled to the distal end of the body, the distal region including a distal end;

a coupler rotatably disposed within the housing, the coupler having a proximal region and a distal region, the coupler including a sealing groove disposed within the distal region, the sealing groove having a bottom surface;

a fixation helix attached to the coupler; and an annular seal disposed within the sealing groove such that the annular seal provides an at least substantially fluid tight seal between the coupler and the housing, the annular seal including:

an annular base portion including a flat side seated against the bottom surface of the sealing groove and an angled side extending obliquely relative to the flat side;

an annular wiper portion sealingly engaged with the inner surface of the housing; and a central portion extending between the base portion and the wiper portion, the annular base portion and the angled side of the annular wiper portion extending axially beyond the central portion to define an annular channel between the annular base portion and the annular wiper portion.

8. The implantable lead of claim 7, wherein the annular base portion has a width parallel to the bottom surface of the sealing groove that is greater than a height of the annular seal measured perpendicular to the bottom surface of the sealing groove.

9. The implantable lead of claim 8, wherein the bottom surface of the sealing groove has a width that is greater than or equal to the width of the annular base portion parallel to the bottom surface of the sealing groove.

10. The implantable lead of claim 7, wherein the annular wiper portion includes a first angled side facing towards the inner surface of the housing and a second angled side that partially defines the annular channel.

11. The implantable lead of claim 10, wherein the first angled side of the annular wiper portion includes a sealing surface that sealingly engages the inner surface of the housing, the sealing surface extending along a portion of the first angled side.

12. The implantable lead of claim 11, wherein the annular seal is molded such that the sealing surface is free of parting lines.

13. The implantable lead of claim 11, further comprising a lubricious coating on the sealing surface.

14. An implantable lead configured to carry an electrical signal, the implantable lead comprising:

a flexible body extending between a proximal end and a distal end, the body configured to carry an electrical signal from the proximal end to the distal end; and a distal assembly coupled to the distal end of the body and including:

a housing having a distal region, a proximal region and an inner surface, the proximal region fixedly coupled to the distal end of the body, the distal region including a distal end;

a coupler rotatably disposed within the housing, the coupler having a proximal region and a distal region, the coupler including a sealing groove disposed within the distal region, the sealing groove having a bottom surface;

a fixation helix attached to the coupler; and an annular seal disposed within the sealing groove such that the annular seal provides an at least substantially fluid tight seal between the coupler and the housing, the annular seal including:

an annular base portion including a first angled side facing towards the inner surface of the housing and a second angled side that partially defines the annular channel;

an annular wiper portion sealingly engaged with the inner surface of the housing; and a central portion extending between the base portion and the wiper portion, the annular base portion and the angled side of the annular wiper portion extending axially beyond the central portion.

* * * * *